(12) United States Patent
Manz et al.

(10) Patent No.: US 11,519,848 B2
(45) Date of Patent: Dec. 6, 2022

(54) PHOTOACOUSTIC GAS SENSOR AND PRESSURE SENSOR

(71) Applicant: Infineon Technologies AG, Neubiberg (DE)

(72) Inventors: Johannes Manz, Munich (DE); Christoph Glacer, Munich (DE); David Tumpold, Kirchheim b München (DE)

(73) Assignee: Infineon Technologies AG, Neubiberg (DE)

(*) Notice: Subject to any disclaimer, the term of this patent is extended or adjusted under 35 U.S.C. 154(b) by 142 days.

(21) Appl. No.: 16/905,295

(22) Filed: Jun. 18, 2020

(65) Prior Publication Data

US 2020/0400553 A1 Dec. 24, 2020

(30) Foreign Application Priority Data

Jun. 19, 2019 (EP) .................................... 19181350

(51) Int. Cl.
| | |
|---|---|
| *G01L 9/00* | (2006.01) |
| *G01L 13/02* | (2006.01) |
| *G01N 33/00* | (2006.01) |
| *G01N 21/17* | (2006.01) |
| *G01N 29/24* | (2006.01) |

(52) U.S. Cl.
CPC ........ *G01N 21/1702* (2013.01); *G01L 9/0073* (2013.01); *G01L 13/026* (2013.01); *G01N 29/2425* (2013.01); *G01N 33/0027* (2013.01); *G01N 2021/1704* (2013.01)

(58) Field of Classification Search
CPC .......... G01N 21/1702; G01N 29/2425; G01N 33/0027; G01L 9/0073; G01L 13/026
See application file for complete search history.

(56) References Cited

U.S. PATENT DOCUMENTS

| | | | | |
|---|---|---|---|---|
| 6,082,178 | A * | 7/2000 | Bernstein | ........... G01N 21/1702 73/579 |
| 8,582,788 | B2 * | 11/2013 | Leidl | .................... H04R 1/2838 381/174 |
| 9,609,429 | B2 * | 3/2017 | Reining | ................. H04R 3/005 |
| 10,302,599 | B2 * | 5/2019 | Tumpold | ........... G01N 29/2418 |
| 10,551,356 | B2 * | 2/2020 | Tumpold | ........... G01N 29/2418 |
| 10,739,220 | B2 * | 8/2020 | Johansen | ................ G01L 11/02 |
| 2006/0027021 | A1 * | 2/2006 | Choi | ..................... G01N 29/11 73/579 |
| 2015/0001647 | A1 | 1/2015 | Dehe et al. | |
| 2015/0256940 | A1 * | 9/2015 | Dehe | ..................... H04R 19/005 381/174 |
| 2018/0038754 | A1 | 2/2018 | Marsh | |
| 2018/0120266 | A1 * | 5/2018 | Tumpold | ............... G01N 29/36 |
| 2019/0039884 | A1 | 2/2019 | Dehe et al. | |

FOREIGN PATENT DOCUMENTS

EP 3483589 A1 5/2019

\* cited by examiner

*Primary Examiner* — Nimeshkumar D Patel
*Assistant Examiner* — Jean F Morello
(74) *Attorney, Agent, or Firm* — Slater Matsil, LLP

(57) ABSTRACT

A MEMS photoacoustic gas sensor includes a first membrane and a second membrane opposing the first membrane and spaced apart from the first membrane by a sensing volume. The MEMS photoacoustic gas sensor includes an electromagnetic source and communication with the sensing volume to deflect the first membrane and the second membrane.

12 Claims, 9 Drawing Sheets

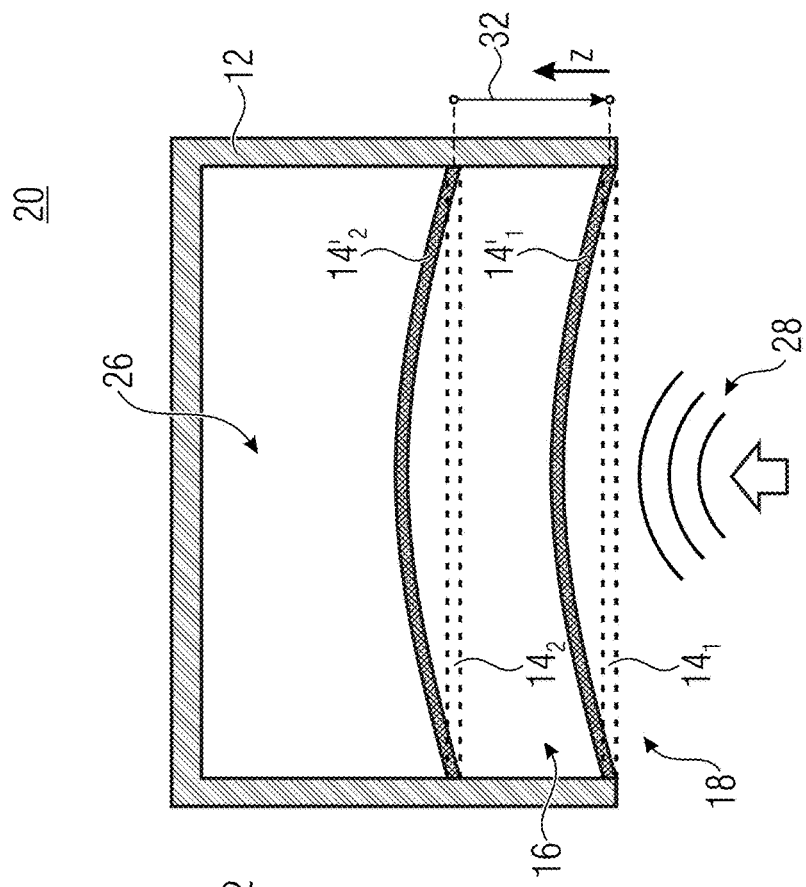
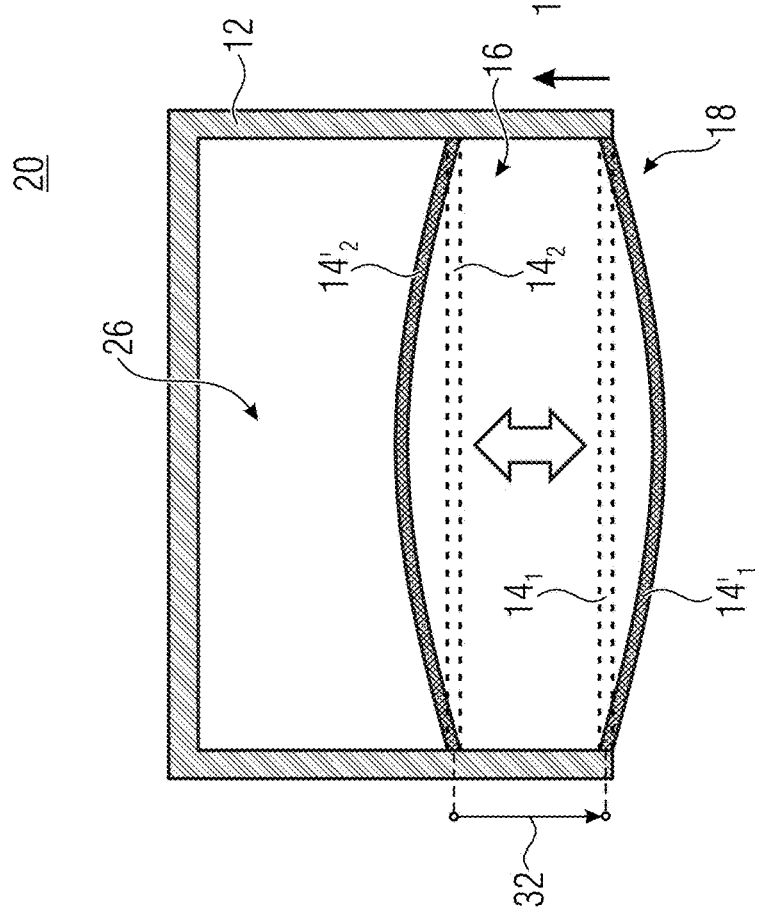

US 11,519,848 B2

PHOTOACOUSTIC GAS SENSOR AND PRESSURE SENSOR

This application claims the benefit of European Patent Application No. 19181350, filed on Jun. 19, 2019, which application is hereby incorporated herein by reference.

TECHNICAL FIELD

The present disclosure relates to a MEMS photoacoustic gas sensor and to a MEMS pressure sensor. The present disclosure further relates to a double membrane photoacoustic spectrometer (PAS) sensor.

BACKGROUND

The sensing of environmental parameters, such a noise, sound, temperature and gases gains more and more importance with mobile devices, home automation and the automotive sector. Harmful gas concentrations can occur due to pollution and malfunction of certain devices. At the same time, well-being is strongly influenced by the air quality. Gas detection by cheap, always available and connected sensors is thus an upcoming topic.

It is thus an object of embodiments to provide for devices that allow for precise measurements of environmental parameters.

SUMMARY

According to an embodiment, a microelectromechanical system (MEMS) photoacoustic gas sensor comprises a first membrane and a second membrane that opposes the first membrane and that is spaced apart from the first membrane by a sensing volume. The MEMS photoacoustic gas sensor comprises an electromagnetic source in communication with the sensing volume. By use of a membrane structure that has two membranes that are adapted so as to both move or deflect, wherein the movement is directed in opposing directions such that the membranes move towards each other or away from each other, a high signal amplitude may be obtained that allows to precisely determine environmental parameters with the photoacoustic gas sensor.

Embodiments provide for a MEMS pressures sensor that comprises a first membrane and a second membrane spaced apart from the first membrane by a sensing volume. The MEMS pressure sensor comprises a circuit configured to measure the capacitance between the first membrane and the second membrane. Again, by having two deflectable membranes that deflect in opposing directions allows for precise measurements of environmental parameters, i.e., a pressure.

Further embodiments are defined in the dependent claims.

BRIEF DESCRIPTION OF THE DRAWINGS

Embodiments are described herein making reference to the appended drawings, in which:

FIG. 2a shows a schematic side view of a part of a MEMS photoacoustic gas sensor according to an embodiment having a back volume in addition to a front volume;

FIG. 2b shows a schematic side view of the parts of the MEMS photoacoustic gas sensor of FIG. 2a being subject to disturbances arriving through the front volume;

Figure 1:
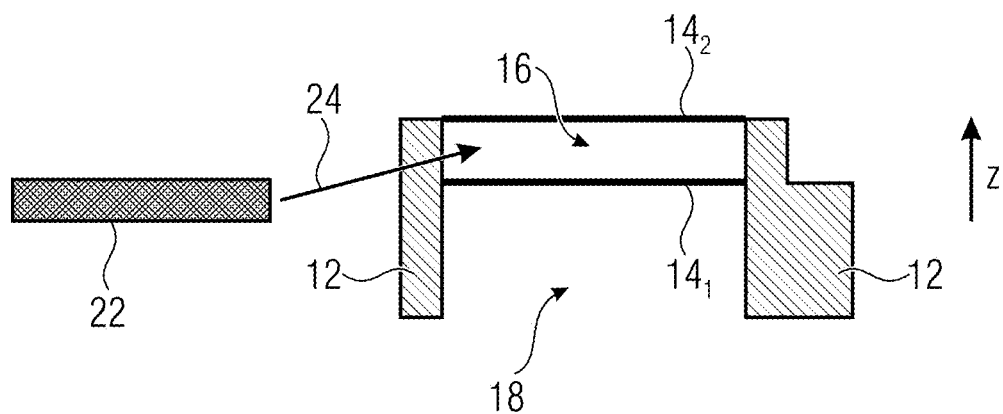
FIG. 1 shows a schematic block diagram of a MEMS photoacoustic gas sensor according to an embodiment.

Equal or equivalent elements or elements with equal or equivalent functionality are denoted in the following description by equal or equivalent reference numerals even if occurring in different figures.

DETAILED DESCRIPTION OF ILLUSTRATIVE EMBODIMENTS

In the following description, a plurality of details is set forth to provide a more thorough explanation of embodiments. However, it will be apparent to those skilled in the art that embodiments may be practiced without these specific details. In other instances, well-known structures and devices are shown in block diagram form rather than in detail in order to avoid obscuring embodiments. In addition, features of the different embodiments described hereinafter may be combined with each other, unless specifically noted otherwise.

In the following, reference is made to measuring an environmental parameter. Some embodiments are directed to measure a concentration of a specific gas and/or a presence of a specific substance or material in a gas. Such measurements may be performed by use of a microelectromechanical system (MEMS) implemented as a photoacoustic gas sensor. This may also be referred to as a photoacoustic spectrometer (PAS) sensor. Such a sensor may be used for gas sensing and may comprise a back volume, a sensing volume and two membranes in between. A certain type of gas being arranged in the sensing volume, at least in a concentration or as a pure gas, may be excited by use of radiation so as to dynamically lead to a deflection of the membranes. Such a deflection may be evaluated and may be associated with the specific gas. I.e., different gases or different concentrations therein may lead to a different behavior of the membranes, the different behavior being measured and thus allowing to conclude the gas or the concentration thereof between the membranes.

FIG. 1 shows a schematic block diagram of a MEMS photoacoustic gas sensor 10 according to an embodiment. The MEMS photoacoustic gas sensor 10 may comprise a substrate 12 that may be formed, at least in part, by use of semiconductor material. For example, the substrate 12 may comprise a silicon material. Alternatively or in addition, the substrate 12 may comprise different semiconductor materials such as gallium arsenide or the like. The substrate 12 may be formed or shaped by use of additive processes, for example, growing respective structures. Alternatively or in addition, subtractive processes may be used, for example, etching processes such that the structure of the substrate 12 remains from a larger body.

The MEMS photoacoustic gas sensor comprises a first membrane $14_1$ and a second membrane $14_2$ opposing the membrane $14_1$. Membranes $14_1$ and $14_2$ may be spaced apart from each other by a sensing volume 16. The sensing volume 16 may allow a gas or particles thereof to travel from a front volume 18 outside the sensing volume 16 into the sensing volume 16, for example, based on diffusion and/or based on slow exchange of gases between the front volume 18 and the sensing volume 16, wherein slow refers to a speed that is understood as non-acoustic.

The MEMS photoacoustic gas sensor 10 comprises an electromagnetic source 22 in communication with the sensing volume 16. The electromagnetic source may be configured to generate and/or emit energy 24 into the sensing volume 16, thereby exciting gas and/or particles in the sensing volume 16. That is, the electromagnetic source may be configured and/or arranged to deflect the first membrane $14_1$ and/or the second membrane $14_2$. Both membranes $14_1$ and $14_2$ may be deflectable with respect to the substrate, for example, along a same direction z. By exciting the sensing volume 16, movements of the membranes $14_1$ and $14_2$ may be generated that oppose each other. For example, the membrane $14_1$ may be deflected along a negative z-direction whilst, at the same time, the membrane $14_2$ is deflected along a positive z-direction due to an expansion inside the sensing volume 16. Alternatively, the membrane $14_1$ may move along positive z-direction whilst, at the same time, membrane $14_2$ moves along negative z-direction.

The electromagnetic source 22 may be configured to emitting the energy 24 dynamically so as to generate dynamic movement of the membranes $14_1$ and $14_2$ such that the described movement may be understood as vibration of membranes $14_1$ and $14_2$, wherein the respective vibration is generated so as to show an inverted direction with regard to the respective other membrane $14_1$ or $14_2$.

Evaluating the opposing movements, for example, by evaluating a voltage or a capacitance between the membranes $14_1$ and $14_2$ may allow for precise measurements with regard to the sensing volume 16 by having a high magnitude of relative movement when compared to a movement of only one movable or deflectable membrane with regard to a stator electrode. At the same time, the structure allows for a high robustness against acoustic noise that may travel to the membrane arrangement $14_1$ and $14_2$, for example, through the front volume 18. Such an acoustic noise, e.g., a sound pressure, may lead to a deflection of membranes $14_1$ and $14_2$ along a same direction and may thus easily be discriminated from the movement generated by the electromagnetic source 22, which allows for a simple compensation.

The membranes $14_1$ and $14_2$ may comprise semiconductor material, for example, a silicon material, e.g., crystalline or polycrystalline silicon. The semiconductor material may be a doped semiconductor material so as to obtain a conductive electrical property that allows a use of the structure as an electrode. Alternatively or in addition, a conductive layer may be arranged at the semiconductor material, for example, a layer comprising a metal material, for example, gold, silver, aluminum, copper or the like.

The electromagnetic source 22 may be configured to generate and/or emit the energy 24 as an electromagnetic energy. For example, the electromagnetic source 22 may be implemented as an infrared source that is configured to emit the energy 24 as an infrared signal. For example, the electromagnetic source 22 may be a heater. The electromagnetic source 22 may comprise conductive material, for example, a doped silicon material or a conductive material arranged at a surface of a substrate material, configured to increase a temperature responsive to an electric current.

FIG. 2a shows a schematic side view of a part of a MEMS photoacoustic gas sensor 20 according to an embodiment having, when compared to the MEMS photoacoustic gas sensor 10, a back volume 26 in addition to the front volume 18. A difference between the front volume 18 and the back volume 26 may be that fluids or gases to be measured as well as disturbances may arrive at the membranes $14_1$ and $14_2$ at the front volume 18 whilst being blocked, at least partially, to a high amount or completely through the back volume 26. The heater 22 is part of the MEMS photoacoustic gas sensor 20 but not shown in FIG. 2a.

In FIG. 2a, the membranes $14_1$ and $14_2$ are also shown in a deflected state $14'_1$ and $14'_2$ that may be obtained by way of excitation through the electromagnetic source 22.

To avoid high pressures in the back volume 26, the substrate 12 forming the back volume 26 may comprise one or more openings that allow for an airflow.

In other words, a photoacoustic signal may generate pressure inside the sensing volume 16. This may lead to a movement of the membranes in opposite directions.

FIG. 2b shows a schematic side view of the parts of the MEMS photoacoustic gas sensor 20 of FIG. 2a being subject to disturbances 28 arriving through the front volume 18. The disturbances 28 may comprise an external pressure, for example, sound pressure or the like. The disturbances 28 may lead to a deflection $14'_1$ and $14'_2$ of the membranes $14_1$ and $14_2$ along a same direction, for example, positive z. This movement may, compared to the opposing movement in FIG. 2a, remain without significant influence on the measured values of a measurement signal 32 between the membranes $14_1$ and $14_2$. For example, when compared to FIG. 2a, the movement in FIG. 2b may leave an electrical capacitance between the membranes $14_1$ and $14_2$ unchanged or may lead to a minor change, wherein the movement of FIG. 2a may lead to a significant change that may easily be determined in the measurement signal 32.

That is, the specific design of MEMS photoacoustic gas sensors described herein can be used to cancel out acoustic noise. Embodiments relate to so-called open system PAS sensor concepts and reduce a sensitivity of such systems to acoustic noise.

According to an embodiment, the MEMS photoacoustic gas sensor 20 is adapted such that a mechanical stiffness of the membrane $14_1$ and a mechanical stiffness of the membrane $14_2$ is implemented differently, i.e., the mechanical stiffnesses may vary with respect to each other. For example, the mechanical stiffnesses may be selected such that an acoustic signal, e.g., the disturbance 28, traveling from the front volume 28 through the sensing volume 16 to the back volume 26 leads to a same magnitude of deflection of the membrane $14_1$ and the membrane $14_2$ within a tolerance range of, for example, ±10%, ±7% or ±5%. For example, an attenuation of an acoustic signal by the membrane $14_1$ and the sensing volume 16 which reduces a mechanical force on the membrane $14_2$ may easily be determined and may be considered by selecting the mechanical stiffness of the membrane $14_1$ and/or $14_2$ so as to have, at least for a reference force magnitude, a same deflection, at least within the tolerance range.

In other words, the pressure of an acoustic signal may lead to a movement of the membranes in a same direction. A photoacoustic signal and an acoustic signal can easily be distinguished.

Figure 3:
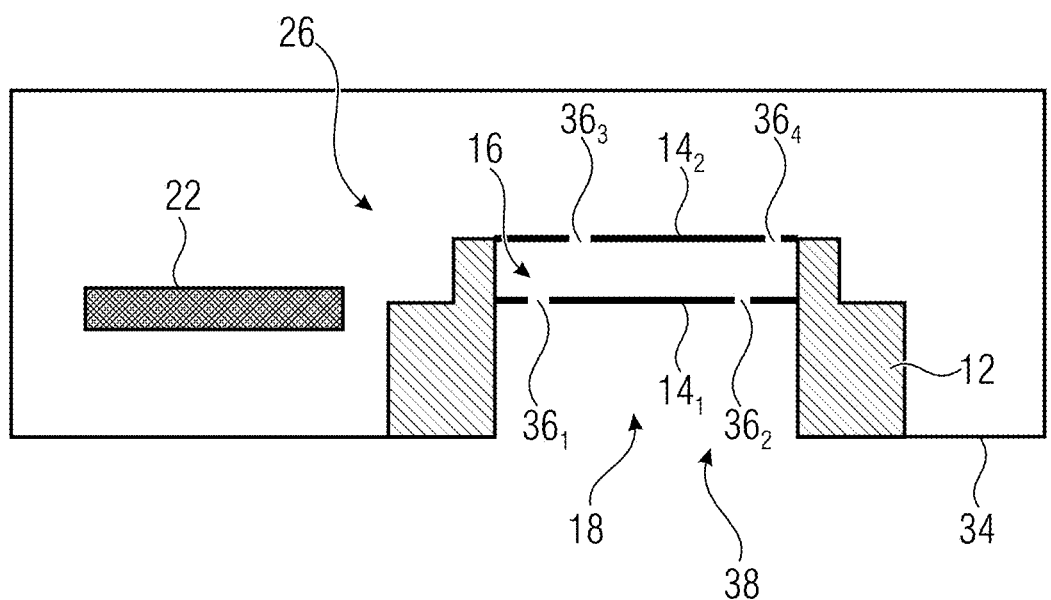
FIG. 3 shows a schematic side view of a MEMS photoacoustic gas sensor according to an embodiment, having a so-called bottom-port configuration.

FIG. 3 shows a schematic side view of a MEMS photoacoustic gas sensor 30 according to an embodiment. The sensing volume may be arranged between the volumes 18 and 26 that are shown, by way of example, as a so-called bottom-port configuration, i.e., the front volume 18 is arranged below the back volume 26, the sensing volume 16 respectively. It is to be noted that expressions like left, right, below or above are used for explanations only, as by rotating a device, the meaning of such description may be changed easily. For example, the MEMS photoacoustic gas sensor 30 may be amended so as to close a housing 34 in the region of the front volume 18 and by opening the housing 34 such that gases and/or disturbances may arrive at the membranes $14_1$ and $14_2$ through the back volume 26, thereby changing the configuration to a top-port configuration and interchanging the meaning of the front volume and the back volume.

Alternatively or in addition, the membrane $14_1$ and/or the membrane $14_2$ may comprise openings, e.g., ventilation holes $36_1$ to $36_4$ in a number of one or more, five or more, ten or more, or even higher for each membrane $14_1$ and $14_2$.

The optional one or more openings $36_1$ and $36_2$ in the membrane $14_1$ may fluidly couple the front volume 18 with the sensing volume 16, i.e., an exchange of fluid, i.e., gas, may occur or happen between the volumes 16 and 18. The exchange of gas molecules may be adapted, e.g., by a number and/or size of the openings $36_1$ and/or $36_2$ to allow a transport of gas molecules, in particular the gas molecules to be detected with MEMS photoacoustic gas sensor. Alternatively or in addition, the one or more openings $36_3$ and $36_4$ in the membrane $14_2$ may fluidly couple the back volume 26 with the sensing volume 16. According to an embodiment, the openings $36_1$ to $36_4$ are each formed with a size so as to block acoustic frequencies. A number and a common, groupwise different or even individual size of openings may be designed in a way that an optimization is obtained to block acoustic frequencies and to allow gas diffusion into the sensing volume. For example, a tradeoff may be made between one or more large openings for fast gas exchange and small openings for good blocking of the acoustic frequencies. The opening allows to exchange fluid to the sensing volume 16 and thus allow for modified measurements in modified environments whilst avoiding acoustic short circuits so as to allow measurements with high quality.

As shown in FIGS. 1, 2a, 2b and 3, the substrate 12 may comprise an opening 38 and may additionally support the membranes $14_1$ and $14_2$ in a way that the membranes $14_1$ and $14_2$ overlay the opening 38.

Figure 4:
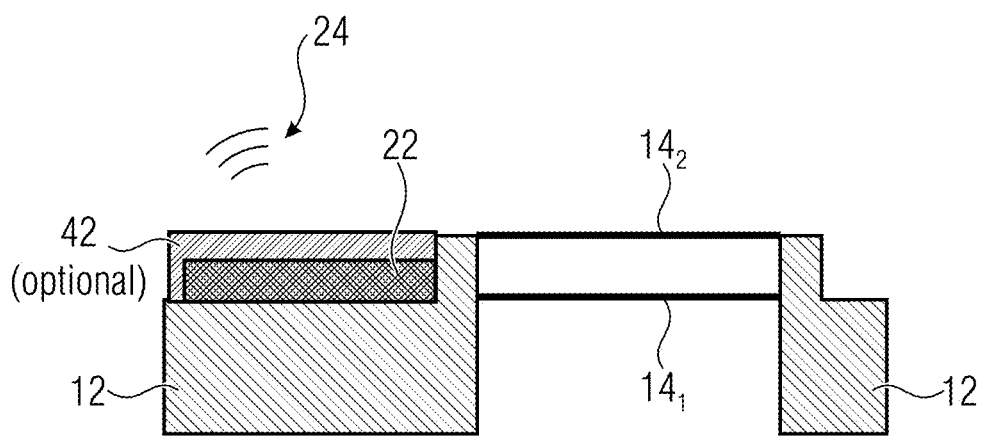
FIG. 4 shows a schematic side view of a MEMS photoacoustic gas sensor according to an embodiment, wherein an electromagnetic source is supported by a semiconductor substrate.

FIG. 4 shows a schematic side view of a MEMS photoacoustic gas sensor 40 according to an embodiment, wherein the electromagnetic source 22 is supported by the semiconductor substrate 12. This allows to obtain compact devices on the one hand and to generate a direction along which the energy 24 is emitted on the other hand. For example, the semi-conductor substrate may act as a reflector or director for the energy 24. Optionally, the electromagnetic source may be covered with a covering layer 42, for example, a filter effective for a specific wavelength to be filtered out or to be led through. Alternatively or in addition, the covering layer 42 may provide for a chemical and/or electrical and/or physical protection of the electromagnetic source 22.

Figure 5:
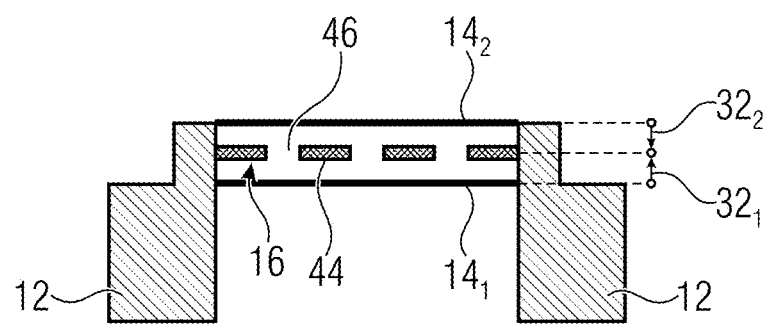
FIG. 5 shows a schematic side view of parts of a MEMS photoacoustic gas sensor according to an embodiment, comprising a backplate structure.

FIG. 5 shows a schematic side view of parts of a MEMS photoacoustic gas sensor 50 according to an embodiment. The MEMS photoacoustic gas sensor 50 may comprise an electrode structure 44, e.g., a backplate structure that may be regarded as immobile when compared to the movable or deflectable membranes $14_1$ and $14_2$. The backplate structure 44 may be arranged between the membranes $14_1$ and $14_2$ in the sensing volume 16. By implementing the backplate structure 44 as a further electrode, two measurement signals $32_1$ and $32_2$ may be measured independently between the membrane $14_1$ and the backplate structure 44, between the membrane $14_2$ and the backplate structure 44 respectively. This may allow for a high precision of the measurements. The backplate structure 44 may comprise openings 46 that may have a size which is comparatively large when compared to the openings 36 so as to avoid an acoustic blocking, in particular so as to prevent generation of pressures between the membranes $14_1$ and $14_2$ and the backplate structure 44.

As described in connection with different MEMS photoacoustic gas sensors, the MEMS photoacoustic gas sensor 50 comprises a non-shown electromagnetic source 22 and may further be arranged such that the sensing volume 16 is arranged between a first and a second volume, e.g., a front volume and a back volume.

Figure 6:
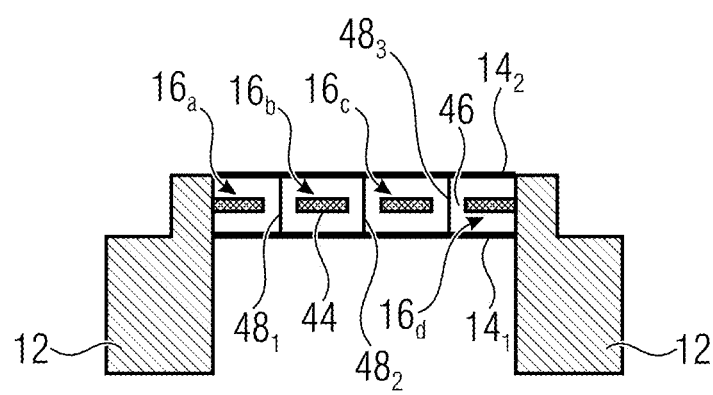
FIG. 6 shows a schematic side view of parts of a further MEMS photoacoustic gas sensor, according to an embodiment.

FIG. 6 shows a schematic side view of parts of a MEMS photoacoustic gas sensor, i.e., the electromagnetic source 22 is not shown. When compared to the MEMS photoacoustic gas sensor 50, the MEMS photoacoustic gas sensor 60 may comprise connectors $48_1$ to $48_3$ mechanically coupled between the membranes $14_1$ and $14_2$. The connectors $48_1$ to $48_3$ may, for example, travel through the openings 46 of the backplate structure 44. Alternatively, the MEMS photoacoustic gas sensor 60 may be implemented without the backplate structure 44. In both configurations, the MEMS photoacoustic gas sensor 60 allows a low amount of deflection in a region of the connectors $48_1$ to $48_3$.

Optionally, the connectors may divide the sensing volume 16 into a plurality of partial sensing volumes 16a-16d. The electromagnetic source may be configured to cause alternating bowings of the adjacent or neighbored parts of the membranes $14_1$ and $14_2$ in adjacent partial sensing volumes. For example, the membranes $14_1$ and $14_2$ may deflect towards each other in one of the partial sensing volumes 16a-16d and may deflect away from each other in an adjacent partial sensing volume. To cause alternating bowings, the electromagnetic source may be controlled so as to provide a transient power signal that may vary in amplitude and/or time, e.g. a sinusoidal signal or a rectangular chopped signal. A number of partial sensing volumes 16a-16d may be arbitrary and may be selected, for example, by mechanical parameters. For example, a distance between the connectors $48_1$ to $48_3$ may be selected such that bowings of a maximum or minimum amplitude occur in the partial sensing volumes.

Alternatively or in addition, a distance between the connectors $48_1$ to $48_3$ and/or a size of the partial sensing volume 16a-16d may be selected under consideration of a resonance frequency that is obtained based on the size of the partial sensing volume 16a-16d. The connectors $48_1$ to $48_3$, that may be arranged in any number and/or any geometry, may be electrically insulating or may, alternatively, be electrically conductive.

Figure 7:
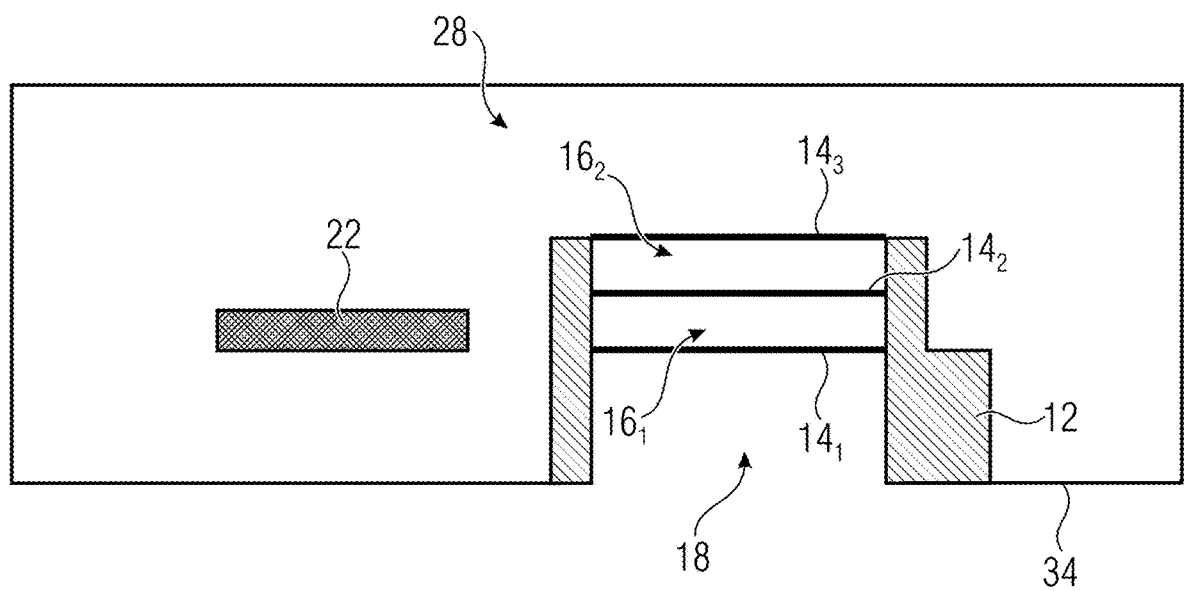
FIG. 7 shows a schematic side view of a MEMS photoacoustic gas sensor according to an embodiment comprising at least a third membrane.

FIG. 7 shows a schematic side view of a MEMS photoacoustic gas sensor 70 according to an embodiment. When compared to the MEMS photoacoustic gas sensors 10, 20, 30, 40, 50 and 60, the MEMS photoacoustic gas sensor 70 may comprise at least a third membrane $14_3$ arranged so as to oppose the membrane $14_2$ and so as to form an additional sensing volume $16_2$, adding to the sensing volume $16_1$ between the membranes $14_1$ and $14_2$. The sensing volumes $16_1$ and $16_2$ may differ from each other, for example, in view of a size and/or in view of gases contained therein or materials for which the sensing volumes $16_1$ and $16_2$ are sensitive. For example, in different sensing volumes $16_1$ and $16_2$, different measurements may be performed. Optionally, the MEMS photoacoustic gas sensor 70 may comprise a further electromagnetic source, configured to emit a respective energy in a different energy level, in a different wavelength range or at different frequencies simultaneously or in different times when compared to the electromagnetic source 22.

The MEMS photoacoustic gas sensor 70 may, as the MEMS photoacoustic gas sensors 10, 20, 30, 40, 50 and/or 60, be formed of a same, single chip by layering and structuring of semiconductor material.

According to an embodiment, the sensing volumes $16_1$ and $16_2$ may be arranged adjacent to each other, divided by the membrane $14_2$. According to another embodiment, the sensing volumes $16_1$ and $16_2$ may be arranged spaced to each other, e.g., by arranging a further, fourth membrane such that the two sensing volumes $16_1$ and $16_2$ may be excited independently from each other as each of the sensing volumes is enclosed by a pair of membranes that is exclusively associated with the sensing volume. Alternatively, by arranging a fourth or even a higher number of membranes, a higher number of sensing volumes may be generated.

In one or more sensing volumes $16_1$ and $16_2$ a backplate structure may be arranged.

Figure 8:
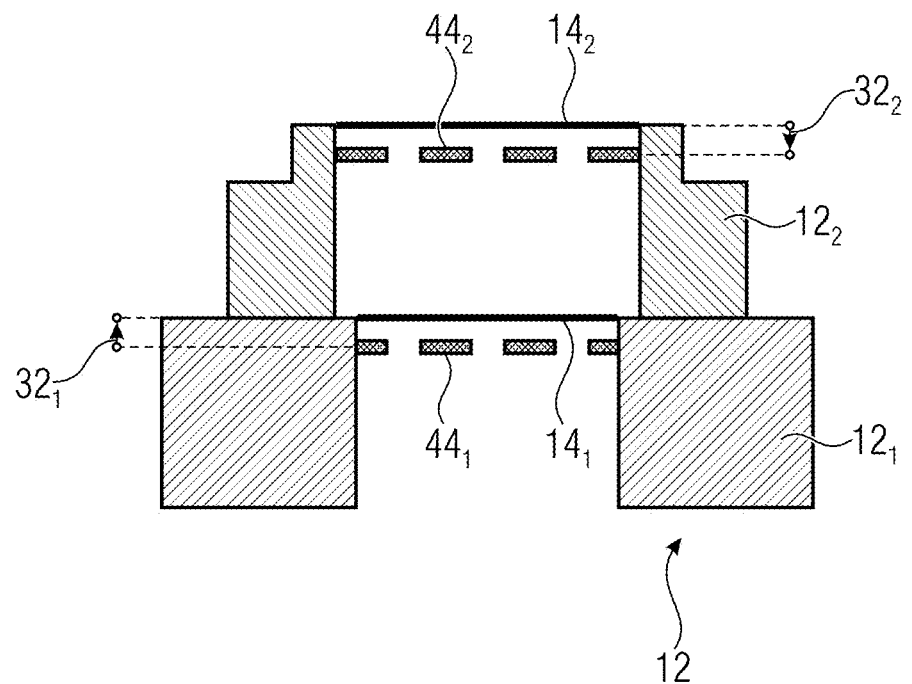
FIG. 8 shows a schematic side view of a part of a MEMS photoacoustic gas sensor according to an embodiment, implemented so as to independently measure a deflection of membranes against immobile backplate structures.

FIG. 8 shows a schematic side view of a part of a MEMS photoacoustic gas sensor 80, in which the electromagnetic source 22 is, again, not shown. When compared to other MEMS photoacoustic gas sensors described herein, the MEMS photoacoustic gas sensor 80 may be implemented so as to independently measure a deflection of the membrane $14_1$ against an immobile backplate structure $44_1$ and to additionally measure the deflection of the membrane $14_2$ against a further immobile backplate structure $44_2$. A position below or above the respective membrane $14_1$, $14_2$ respectively of the associated backplate structure $44_1$, $44_2$ respectively may be selected independently. This may allow for a high selectivity of when evaluating measurement results. This also allows for fabricating a first, e.g., upper, group (membrane $14_2$, the immobile backplate structure $44_2$ and the adjacent substrate $12_2$) and a second, e.g., lower, group (membrane $14_1$, the immobile backplate structure $44_1$ and the adjacent substrate $12_1$) to be fabricated in separate fabrication processes. The groups may, for example, then be joined together with a joining process.

Figure 9:
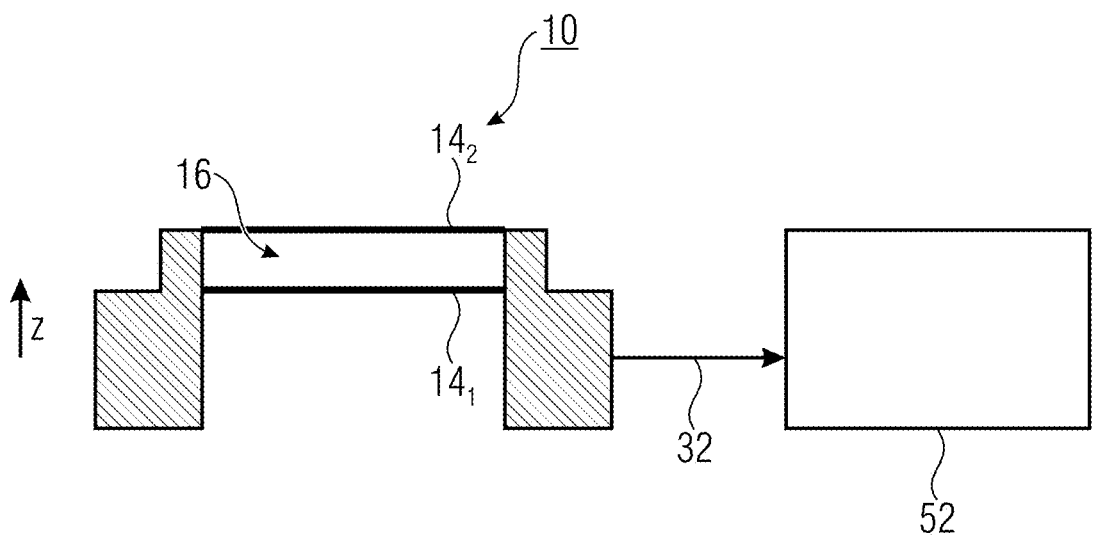
FIG. 9 shows a schematic side view of a part of a MEMS photoacoustic gas sensor according to an embodiment comprising a circuit.

FIG. 9 shows a schematic side view of a part of a MEMS photoacoustic gas sensor 90 according to an embodiment. For example, the MEMS photoacoustic gas sensor 90 may comprise the MEMS photoacoustic gas sensor 10, wherein, alternatively or in addition, any other MEMS photoacoustic gas sensor described herein may be arranged. Additionally, the MEMS photoacoustic gas sensor 90 comprises a circuit, for example, a processor such as a central processing unit (CPU) or a microcontroller or an application specific integrated circuit (ASIC) or a field programmable gate array (FPGA) configured to process at least one signal, e.g., the measurement signal 32, generated by the deflections of the membranes $14_1$ and $14_2$. For example, the circuit 52 may be configured to associate the measurement signal 32 with properties of a fluid in the sensing volume 16.

Embodiments described herein are described in connection with the MEMS photoacoustic gas sensors. According to further embodiments, a MEMS pressure sensor is provided. As described in connection with the MEMS photoacoustic gas sensors, a MEMS pressure sensor in accordance with embodiments may comprise a first and a second membrane that are spaced apart from each other so as to form a sensing volume therebetween. The pressure sensor may comprise a circuit configured to measure the capacitance between the first membrane and the second membrane, for example, by use of the circuit 52. That is, instead of evaluating a deflection of the membranes $14_1$ and $14_2$ in opposing directions, a deflection along a same direction may also be evaluated, wherein this deflection may be associated to a pressure acting on the sensing volume 16.

PAS sensors described herein may comprise a sensing volume and a back volume and, optionally, a front volume. Between the back volume and the sensing volume a membrane is placed. Between the sensing volume and the environment (front volume) a second membrane is placed. The movement of the membranes may be coupled, mechanically, e.g., by use of connectors, or by the intermediate air or fluid. Due to the arrangement of the membranes, a photoacoustic signal may be distinguished from acoustic noise. When compared to a solution with a second device used for cancelling out acoustic noise, embodiments allow to obtain precise measurements with a same device thereby avoiding a need for additional devices used for correction. Optionally, the electromagnetic source, e.g., the infrared emitter, and the two membranes may be realized in one chip resulting in a small package size.

Embodiments may comprise three, possibly major components, that are connected in a setup that may easily be built and that may enhance the functionality of sensors. A first component is a bulk silicone frame with a Bosch hole to generate a cavity for the membranes. A second component may be a first membrane or thin structure which is aligned on the cavity or hole of the first component. A further, third component may be a second membrane or thin structure which is aligned on the cavity or hole described in connection with the first component. This membrane is located above the first membrane.

Optionally, additional components may be added. Amongst those, there is a backplate structure between the membranes for a more sophisticated readout. Alternatively or in addition, connecting elements may be arranged between the membranes to enhance uniform movement of the membranes under the impact of acoustic noise, e.g., the connectors.

Embodiments allow for a detection of a membrane movement which is realized by capacitive, piezo or inductive readout. Gas diffusion into the sensing volume may be realized by ventilation holes in both membranes. The same ventilation holes may be used for static pressure compensation. Optionally, an emitter is placed on the same chip aside to the stack of membranes.

Further in the text: The described embodiments may form a sensing subpart, i.e., a component, of a Photo Acoustic Spectrometer (PAS) sensor. The setup can also be used as a slow transient pressure sensor. In the targeted PAS sensor, the readout may be realized via a pressure sensitive membrane. To distinguish the wanted sensor signal from noise, a differential readout may be implemented, using two membranes. Embodiments are directed to a concept, sensors and methods, to realize the differential readout via two membranes which are located on one after another (in contrast to be arranged side by side). The sensing volume may be arranged in between the membranes. Acoustic noise may lead to a deflection of the membranes in the same direction, whereas a photoacoustic signal may lead to a deflection in opposing directions. By this, a noise signal and a sensor signal can be distinguished.

Embodiments allow to obtain small and miniaturized PAS sensors. Such sensors can be used in environments with acoustic noise, e.g., speech, music, ambient noise or the like.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

The above described embodiments are merely illustrative for the principles of the present disclosure. It is understood that modifications and variations of the arrangements and the details described herein will be apparent to others skilled in the art. It is the intent, therefore, to be limited only by the scope of the impending patent claims and not by the specific details presented by way of description and explanation of the embodiments herein.

What is claimed is:

1. A MEMS photoacoustic gas sensor, comprising:
a housing enclosing:
a first membrane;
a second membrane opposing the first membrane and spaced apart from the first membrane by a sensing volume; and
an electromagnetic source in communication with the sensing volume,
wherein the first membrane is supported by a semiconductor substrate having an opening through the housing, the first membrane overlying the opening, wherein the electromagnetic source is supported by the semiconductor substrate, and wherein the electromagnetic source is an infrared source comprising a heater, and
wherein the first membrane is disposed between the sensing volume and a first volume, and the second membrane is disposed between the sensing volume and a third volume, wherein the first volume is a front volume and the third volume is a back volume; or wherein the first volume is a back volume and the third volume is a front volume, wherein a first stiffness of the first membrane and a second stiffness of the second membrane are selected such that an acoustic signal travelling from the front volume through the sensing volume to the back volume leads to a same magnitude of deflection of the first membrane and the second membrane within a tolerance range, and wherein the first stiffness is different than the second stiffness.

2. The sensor according to claim 1, wherein the first membrane includes at least one first opening fluidly coupling the first volume and the sensing volume, and the second membrane includes at least one second opening fluidly coupling the third volume and the sensing volume.

3. The sensor of claim 2, wherein the at least one first opening and the at least one second opening are differently sized.

4. The sensor according to claim 1, further comprising a backplate disposed between and spaced apart from the first membrane and the second membrane.

5. The sensor according to claim 1, further comprising one or more connectors mechanically coupled between the first membrane and the second membrane.

6. The sensor of claim 5, wherein the one or more connectors are electrically conductive.

7. The sensor of claim 5, wherein the one or more connectors are electrically insulating.

8. The sensor according to claim 5, wherein the one or more connectors divide the sensing volume into a plurality of partial sensing volumes, the electromagnetic source configured to cause alternating bowings of the first membrane and the second membrane in adjacent partial sensing volumes.

9. The sensor according to claim 1, wherein the sensing volume is a first sensing volume, wherein the sensor comprises at least a third membrane forming at least a part of a stack with the first membrane and the second membrane and defining a second sensing volume in the stack.

10. The sensor according to claim 1, further comprising a circuit configured to process at least one signal generated by a first deflection of the first membrane and a second deflection of the second membrane.

11. A MEMS pressure sensor, comprising:
the sensor according to claim i; and
a circuit configured to measure a capacitance between the first membrane and the second membrane.

12. The sensor according to claim 1, wherein the tolerance range is $\pm_5\%$.

* * * * *

UNITED STATES PATENT AND TRADEMARK OFFICE
CERTIFICATE OF CORRECTION

PATENT NO. : 11,519,848 B2
APPLICATION NO. : 16/905295
DATED : December 6, 2022
INVENTOR(S) : Johannes Manz It is certified that error appears in the above-identified patent and that said Letters Patent is hereby corrected as shown below:

In the Claims

Claim 11, Column 10, Line 40; delete "i" and insert --1--.

Signed and Sealed this
Thirty-first Day of January, 2023

Katherine Kelly Vidal
*Director of the United States Patent and Trademark Office*